(12) United States Patent
Pylkkanen

(10) Patent No.: US 8,679,364 B2
(45) Date of Patent: Mar. 25, 2014

(54) DEICER COMPOSITIONS AND PROCESSES FOR MAKING DEICERS

(71) Applicant: API Intellectual Property Holdings, LLC, Atlanta, GA (US)

(72) Inventor: Vesa Pylkkanen, Atlanta, GA (US)

(73) Assignee: API Intellectual Property Holdings, LLC, Atlanta, GA (US)

(*) Notice: Subject to any disclaimer, the term of this patent is extended or adjusted under 35 U.S.C. 154(b) by 0 days.

(21) Appl. No.: 13/968,892

(22) Filed: Aug. 16, 2013

(65) Prior Publication Data

US 2013/0334456 A1 Dec. 19, 2013

Related U.S. Application Data

(62) Division of application No. 13/621,903, filed on Sep. 18, 2012.

(60) Provisional application No. 61/536,477, filed on Sep. 19, 2011.

(51) Int. Cl.
  *C09K 3/18* (2006.01)
  *C07C 51/00* (2006.01)
  *C07C 51/41* (2006.01)

(52) U.S. Cl.
  CPC ........... *C09K 3/185* (2013.01); *C07C 51/41* (2013.01); *C07C 51/412* (2013.01)
  USPC ............................ 252/70; 106/13; 562/515

(58) Field of Classification Search
  USPC .................................. 106/13; 252/70; 562/515
  See application file for complete search history.

(56) References Cited

U.S. PATENT DOCUMENTS

| | | | | | |
|---|---|---|---|---|---|
| 4,664,832 | A | * | 5/1987 | Sandvig et al. | 252/70 |
| 4,746,449 | A | * | 5/1988 | Peel | 252/70 |
| 4,855,071 | A | * | 8/1989 | Todd et al. | 252/70 |
| 5,254,465 | A | * | 10/1993 | Wise | 435/140 |
| 5,264,623 | A | * | 11/1993 | Oehr et al. | 562/515 |
| 5,376,293 | A | * | 12/1994 | Johnston | 252/70 |
| 6,059,989 | A | * | 5/2000 | Stankowiak et al. | 252/70 |
| 7,938,981 | B2 | * | 5/2011 | Dunuwila et al. | 252/70 |
| 2013/0175467 | A1 | * | 7/2013 | Bradt et al. | 252/70 |

* cited by examiner

*Primary Examiner* — Anthony J Green
(74) *Attorney, Agent, or Firm* — Ryan P. O'Connor

(57) ABSTRACT

The formulation of the current invention provides better deicing and anti-icing performance than commercial acetate-based deicing solutions. The performance is consistently better in all testing categories including melting, penetration, undercutting, and friction. The corrosiveness is similar to commercial deicers, which may include corrosion inhibitors. Chemical analysis reveals that a potassium acetate solution provided by the invention contains formate and lactate in the prepared deicer.

10 Claims, No Drawings

DEICER COMPOSITIONS AND PROCESSES FOR MAKING DEICERS

PRIORITY DATA

This patent application is a divisional application of pending U.S. patent application Ser. No. 13/621,903, filed Sep. 18, 2012, which is a non-provisional application claiming priority to U.S. Provisional Patent App. No. 61/536,477 for "COMPOSITION AND PROCESS OF DEICER SOLUTION" filed Sep. 19, 2011, each of which is hereby incorporated by reference herein.

STATEMENT REGARDING FEDERALLY SPONSORED RESEARCH OR DEVELOPMENT

This invention was made with Government support under Contract No. DE-EE0002868. The Government has certain rights in this invention.

FIELD OF THE INVENTION

This invention relates, in general, to deicer preparation and in particular to manufacture and compositions of acetate-, formate-, and lactate-based deicers from biomass.

BACKGROUND OF THE INVENTION

Snow and ice cause significant hardship in cold climates. Major issues from freezing conditions are the loss of normal friction on surfaces and the buildup of ice. The consequences range from personal slip and fall injuries to collisions on the roadways and to economic losses in conveying material. Especially, the airline sector combats winter conditions to keep runways open and to keep exposed aircraft components from freezing.

Road maintenance crews most often use granular sodium chloride, more commonly referred as "road salt" for deicing. The salt suppresses the freezing point of water and converts ice or snow to ionic solution. The road salt loses its effectiveness completely at below −18° C., which is the freezing point of a saturated sodium chloride solution. Road salt is corrosive to ferrous metals commonly found in the vehicles and structures. Significant economic loss can be attributed to maintenance of transportation infrastructure and reduced life of vehicles due to rusting.

Other inorganic salt replacements have been proposed and tested, including magnesium and calcium chloride. Although some corrosion aspects are avoided, the inorganic salts tend to leave a solid residue on surfaces. Also, surface water and ground water salination are possible results from overuse of the inorganic salts.

Organic deicers, which leave no residue, are used for deicing and anti-icing applications in aircraft as well as vehicles. Common examples of such deicers include ethylene glycol and methanol, which both exhibit toxicity towards human and aquatic life.

Organic salt deicers have gained acceptance in the corrosion-averse applications such airport runway deicing. In the past 20 years, organic salts have replaced urea as the deicer of the choice. Urea is a nitrogen-based chemical, which promotes plant growth. Potassium/sodium acetate is more expensive than sodium chloride. Because of the low corrosiveness of potassium/sodium acetate, the most common use is for airport runway deicers. Recently, they replaced urea as a more environmentally friendly medium. Acetates are biodegradable and do not provide nutrients into surrounding streams and groundwater.

In 2009, U.S. Environmental Agency proposed rule 40 CFR Part 449 (44684 Federal Register/Vol. 74, No. 166/ Friday, Aug. 28, 2009); Effluent Limitation Guidelines and New Source Performance Standards for the Airport Deicing Category. This rule requires large airports performing airfield pavement deicing to use non-urea-based deicers. Based on a 2009 survey of 325 primary airports, the U.S. EPA estimates that most common deicing chemicals are potassium acetate (63 percent); urea (12 percent); propylene glycol-based fluids (11 percent); sodium acetate (9 percent); sodium formate (3 percent); and ethylene glycol-based fluids (2 percent).

North American acetate-based runway deicers are covered in FAA-approved specification SAE AMS 1435A. Because over 90% acetic acid is produced starting from fossil fuel derived sources, the acetate based deicers have a large carbon footprint. U.S. manufacturers include of acetate based deicers include Cryotech Inc.

Potassium formate is commonly used for deicers in European airports. The biological oxygen demand from formate is lower than from acetate. The potassium formate deicer is covered in FAA-approved specification SAE AMS-1431B. Formic acid may be produced as an acetic acid byproduct or by direct synthesis with carbon monoxide and alcohol. European manufacturers of potassium formate-based deicers include Kemira Inc.

One concern in organic salt-based deicers is the oxidation of brake pads in the aircraft. Therefore, corrosion inhibitors are to be added to the formulations. Potassium formate is currently not recommended in the U.S. because of corrosion concern (FAA CERT ALERT NO. 01-04, 19 Dec. 2001).

New green deicer alternatives from biobased sources include propanediol and glycerin byproduct from biofuel production to address corrosiveness and carbon footprint. These were used also to alleviate potassium acetate shortage in the 2009/2010 season, because of a mining strike in Canada.

Peel (U.S. Pat. No. 4,746,449) teaches deicing products obtained from pulp mill black liquor consisting of acetates, formates, and lactates in certain ratios. The cations include calcium, magnesium, sodium and ammonia.

Stankowiak, et al. (U.S. Pat. No. 6,059,989) teach a deicing composition based on acetates and/or formates, and a method for melting snow and ice on traffic areas with the aid of said composition. Stankowiak, et al. list silicate and phosphate as active ingredients.

Improved deicers are needed in the market. What are needed are deicer compositions that mitigate corrosion concerns and have a good environmental lifecycle (such as being produced from biomass), while performing as good as incumbent deicers.

SUMMARY OF THE INVENTION

The present invention addresses the aforementioned needs in the art, as will now be summarized and then further described in detail below.

The present invention describes a process and formulation originating from treatment of biomass, separating organic acids and purifying them to commercial deicer. The deicer consists of mixture of acetic, formic, and lactic acids combined with a selected cation at alkaline pH. Naturally occurring impurities and corrosion inhibitors may be added to meet deicer product specifications.

In some variations, the invention provides a deicer composition comprising an alkali acetate, an alkali formate, and a solvent for the alkali acetate and the alkali formate. The alkali may be selected from the group consisting of potassium, sodium, magnesium, calcium, and combinations thereof. In some embodiments, the alkali is a combination of potassium and sodium. In some embodiments, the alkali is a combination of magnesium and calcium. The solvent may be water, or consist essentially of water, although other solvents could in principle be utilized.

The alkali acetate may be selected from the group consisting of potassium acetate, sodium acetate, magnesium acetate, calcium acetate, and combinations thereof and wherein the alkali formate is independently selected from the group consisting of potassium formate, sodium formate, magnesium formate, calcium formate, and combinations thereof.

In some embodiments, the alkali acetate is present in a concentration from about 30 wt % to about 99 wt %, such as greater than about 50 wt %, e.g. from about 50 wt % to about 99 wt %.

In some embodiments, the alkali formate is present in a concentration from about 1 wt % to about 15 wt %, such as from about 3 wt % to about 12 wt %, or about 6 wt % to about 10 wt %.

In some embodiments, the mass ratio of the alkali formate to the alkali acetate is less than 0.5, such as about 0.3 or less, about 0.2 or less, about 0.1 to about 0.2, or about 0.12 to about 0.18.

In some embodiments, the composition includes from about 25 wt % to about 75 wt % dissolved solids, such as from about 45 wt % to about 65 wt % dissolved solids.

In some embodiments, the deicer composition further comprises one or more corrosion inhibitors. In these or other embodiments, the deicer composition further comprises one or more color-enhancement additives. Impurities may be present, preferably in a concentration of about 1 wt % or less.

Some embodiments of the invention provide a crystallized deicer composition comprising an alkali acetate and an alkali formate. The crystallized deicer composition may be obtained from substantially removing the solvent from the deicer composition as disclosed.

Some embodiments provide a dried deicer composition comprising an alkali acetate and an alkali formate. The dried deicer composition may be obtained from drying a deicer composition as disclosed.

The present invention also provides a process for producing a deicer composition, the process in some variations comprising:

(a) treating a biomass feedstock in the presence of an acidic, neutral, or alkaline solution to solubilize at least a portion of the biomass, thereby producing an extract liquor;

(b) adjusting the pH of the extract liquor to a selected first pH of about 4.8 or less, thereby producing an acidified extract liquor comprising acetic acid and formic acid;

(c) separating dissociated acetic acid and formic acid from the acidified extract liquor to form a dilute organic acid solution;

(d) combining the dilute organic acid solution with an alkali oxide, alkali hydroxide, and/or alkali carbonate, wherein the alkali is selected from the group consisting of potassium, sodium, magnesium, calcium, and combinations thereof, to adjust the pH to a selected second pH of at least about 3.8, thereby producing an organic salt solution comprising alkali acetate and alkali formate; and (e) concentrating the organic salt solution to a concentration of at least about 25 wt % organic salts, thereby producing a deicer composition comprising alkali acetate and alkali formate.

In some embodiments, treating in step (a) comprises extraction using steam or hot water, optionally with one or more additives or catalysts. The first pH may be from about −2 to about 4.8. In some embodiments, the first pH is less than about 3.8, such as from about 2 to about 3. The first pH may be obtained using a strong acid, or by using a heat treatment in the presence of sulfur dioxide and/or carbon dioxide, for example. In some embodiments, the amount of formic acid produced is varied by adjusting the first pH.

In some embodiments, step (c) comprises a separation step selected from the group consisting of vaporization, membrane separation, molecular sieves, and combinations thereof.

The dilute organic acid solution may include from about 0.05 wt % to about 4 wt % acetic acid and from about 0.01 wt % to about 1 wt % formic acid.

In some embodiments, the second pH is at least about 4.8, such as from about 4.8 to about 14, or from about 8 to about 11.

The process may further comprise introducing an additional amount of formic acid or a formate salt to the dilute organic acid solution or to the organic salt solution.

Step (e) may include a separation step selected from the group consisting of membrane separation, evaporation, molecular sieves, and combinations thereof. In some embodiments, the organic salt solution is concentrated in step (e) to a concentration of at least about 50 wt % organic salts. In some embodiments, the organic salt solution is filtered and dried using heat and/or vacuum. The organic salt solution or the deicer composition may be crystallized to at least 99 wt % purity, if desired.

In some embodiments, the process further includes purification of the deicer composition to produce a purified deicer composition, wherein the purification comprises a step selected from the group consisting of ion exchange, activated-carbon treatment, filtration, crystallization, and combinations thereof. The purification may be conducted prior to step (e), or after step (e).

The deicer composition produced may comprise the alkali formate in a concentration from about 1 wt % to about 15 wt %, such as 3-12 wt % or 6-10 wt %. The process may include adding one or more corrosion inhibitors and/or color-enhancement additives to the deicer composition.

The present invention also provides a deicer composition produced by a process as disclosed, and apparatus configured for carrying out the process.

DETAILED DESCRIPTION OF EMBODIMENTS OF THE INVENTION

The compositions, processes, and, systems of the present invention will now be described in detail by reference to various non-limiting embodiments, including the examples which are exemplary only. This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing concentrations, conditions, and so forth used in the specification and claims are to be understood as being modified in all instances by the term "about." Accordingly, unless indicated to the contrary, the numerical parameters set forth in the following specification and attached claims are approximations that may vary depending at least upon an applicable analytical technique. Without limiting the application of the doctrine of equivalents to the scope of the claims, each numerical parameter should at least be construed in light of the number of reported significant digits and by applying ordinary rounding techniques.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of"

The present invention may be practiced by implementing method steps in different orders than as specifically set forth herein. All references to a "step" may include multiple steps (or substeps) within the meaning of a step. Likewise, all references to "steps" in plural form may also be construed as a single process step or various combinations of steps.

As intended herein, the term "deicer" broadly includes deicers, anti-icers, and similar compounds, mixtures, or solutions that are effective to remove ice (e.g., by partial or complete melting), or prevent the formation of ice (e.g., by freezing-point depression of water), with respect to an object or surface. The deicer may function for kinetic reasons, thermodynamic reasons, physical reasons, or combinations thereof. Mechanical devices known in the art as deicers may be utilized along with the deicer compositions provided herein, in some embodiments.

The present inventors have found effective deicer compositions, which originate from the extraction treatment of biomass. After separation of organic acids from the extract and combining with soluble base, the aqueous solution performed better than commercially formulated acetate based deicer. To our surprise, the chemical analysis showed that the composition in some embodiments contains formic and lactic acids. In another example, the deicer contained naturally occurring cations from wood. Another analysis shows trace amount of derivatives originating from sugars and phenolic compounds in wood.

The current invention, in some variations, introduces a formulation of deicer that is a mixture of biomass-derived potassium acetate, potassium formate, and other wood-based derivatives. The formulation has better deicing performance than potassium acetate-based solutions, while having comparable corrosion resistance, in some embodiments.

In some variations, the first step of the method consists of treatment of biomass, such as wood chips, grasses or corn or grains, and most preferably hardwoods, to dissolve at least part of the biomass into acidic, neutral, or alkaline solution. Hemicelluloses, which contain acetyl groups, are easily cleaved in thermal or chemical treatment. One preferred method of extraction is by steam or hot water. Acidic catalysts include organic acids, such as formic acid, acetic acid, or mineral acids including sulfuric acid, hydrochloric acid, nitric acid, sulfurous acid, and sulfur dioxide. Neutral additives include organic alcohols, including methanol, ethanol, butanol, and ketones such as acetone and MEK. Alkaline additives include sodium, potassium, magnesium and calcium oxides/hydroxide/carbonates, urea, and ammonia.

The treatment medium may also be a combination of aforementioned components with small amounts of incidental or deliberate additives, such as anthraquinone. More specifically, the treatments may include current Kraft, Sulfite, Bisulfite, Soda, NSSC, TMP, CTMP, Masonite, and groundwood pulping methods. One may apply the invention in current and future biorefineries, specifically where wood is treated with acid, solvent, water, or alkali to liberate hemicelluloses from the wood. Especially it should be noted that the liberation of acetyl groups can be increased by a secondary chemical or heat treatment of the extract liquor.

The second step of the method, in some variations, is adjustment of the extract liquor at pH 4.8 or below to achieve dissociation point of acetic acid and preferably below 3.8, which is dissociation point formic acid. The pH range is therefore −2 to 4.8 and more preferably between 2 and 3. The acidification may be performed using a strong acid, such as sulfuric, hydrochloric, nitric, or phosphoric acid. The acidification may also be done with sulfur dioxide or carbon dioxide and a heat treatment. It should be noted that the formic acid content may be tuned by changing pH of the treatment of the extract liquor.

The third step of the method, in some variations, separates the dissociated organic acids from the solution by vaporization, by membranes, or by a molecular sieve from the other dissolved wood components. The separation can be done in a single step or multiple steps. This creates a very dilute water-based solution, where acetic acid is present from about 0.05-4 wt % concentration and formic acid is present at about 0.01-1 wt % concentration, for example.

The fourth step of the method, in some variations, is to add an alkali to the dilute organic acid solution. The alkali may be selected from group consisting of sodium, potassium, magnesium, and calcium oxides/hydroxide/carbonates, preferably potassium hydroxide. A mixture of alkalis and metals may be added or cations may originate from the biomass or chemical impurities. Such impurities include organic degradation products and inorganics, such as silicates in the biomass. In some embodiments, the target pH is above the lower dissociation point of 3.8, but preferably between 4.8 and 14, such as 5, 6, 7, 8, 9, 10, 11, 12, or 13, and more preferably between 8 and 11. This ensures that all organic acids are associated with the alkali, forming an organic salt. The formic acid concentration may optionally be standardized by adding a known amount of formic acid up to 50 wt % of the solution, for example. Lactic acid may be present from natural sources or as an additive, such as in concentrations of 0.1 wt %, 0.5 wt %, or 1 wt %.

The fifth step of the method, in some variations, includes concentration of organic salt from the dilute solution. The concentration may be performed by membrane separation, evaporation, or molecular sieves. In some embodiments, the separation is performed by combining at least two aforementioned methods. The final solution may be concentrated to 25-75 wt % or other concentrations, according to deicing transportation and usage requirements. In certain embodiments, the solution is concentrated to approximately 50% strength. In one embodiment of the invention, the organic salt is crystallized to high purity, such as close to or about 100% purity. In another embodiment, the insoluble solids are filtered and dried using heat or vacuum.

The sixth step of the process, in some variations, is purification of the organic salt. The purification may be performed using ion exchange, activated carbon, filtration, or another separation process. The purification may combine several steps to achieve removal of unwanted components. The purification may be performed before and/or after the concentration step.

Some embodiments of the present invention utilize, at least in part, processes described in U.S. Pat. No. 8,211,680 issued Jul. 3, 2012 to Retsina et al., which is hereby incorporated by reference herein. Some embodiments of the present invention utilize, at least in part, processes described in co-pending U.S. patent application Ser. Nos. 13/026,273 or 13/026,280, which are each hereby incorporated by reference herein.

In this description, reference has been made to multiple embodiments. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the principles of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and examples described herein provide an indication of the utility and versatility of the present invention. Other embodiments that do not provide all of the features and advantages set forth herein may also be utilized, without departing from the spirit and scope of the present invention. Such modifications and variations are considered to be within the scope of the principles of the invention defined by the claims.

EXAMPLES

Example 1

Northern hardwood liquid extract from masonite steam explosion process was collected after steaming, refining and washing the residual wood pulp. The extract consisted of approximately 1.0% of dissolved solids and 0.1% of suspended solids (weight basis). After hydrolyzing with 3 wt % sulfuric acid for 1 hour at 120° C., the average acetic acid concentration increased tenfold from 0.04 mg/mL to 0.4 mg/mL. The extract was pumped through a nanomembrane, which concentrated the dissolved solids, but allowed smaller molecules to pass to permeate. About 250 gallons of permeate was neutralized first with sodium hydroxide and potassium hydroxide, respectively. The permeate was pumped at 400 psig through a tight RO membrane to provide 0.89% potassium acetate solution.

Example 2

Corrosion testing of the acetate solution generated in Example 1 was performed using SHRP H-205.7, Test Method for Evaluation of Corrosive Effects of Deicing Chemicals on Metals. The method for this testing can be found in the Strategic Highway Research Program, National Research Council, publication designated SHRP-H-332. This is the Handbook of Test Methods for Evaluating Chemical Deicers. Also referenced for this testing were ASTM G1-91, Standard Practice for Preparing, Cleaning, and Evaluating Corrosion Test Specimens, ASTM G31-72, Standard Method for Laboratory Immersion Corrosion Testing of Metals, ASTM G46-76, Standard Practice for Examination and Evaluation of Pitting Corrosion, and ASTM E70-90, Standard Test Method for pH of Aqueous Solutions with Glass Electrode. The API deicer results compared against a commercial deicer standard are shown in Table 1. The potassium acetate solution from Example 1 is labeled "API KA" (KAc) in Table 1. A solution of sodium acetate, labeled "API NaAc" was also prepared in a similar manner and tested.

The deicers were subjected to a friction test. Table 2 shows the measured coefficient of friction of API KA (potassium acetate deicer) relative to other compounds.

TABLE 1

Corrosion testing against commercial deicer.

| Sample | Metal Type | Time | Start Wt (g) | 1 week Wt (g) | Difference From Start (g) | PH | Comments |
|---|---|---|---|---|---|---|---|
| Commercial KA | Bare Metal | 1 wk | 8.3702 | 8.3694 | −0.001 | 7 | No visible corrosion |
| Commercial KA | Bare Metal | 1 wk | 8.5327 | 8.5322 | −0.001 | 7 | No visible corrosion |
| Commercial KA | Bare Metal | 3 wk | 8.1867 | 8.1839 | −0.003 | 7 | No visible corrosion |
| Commercial KA | Bare Metal | 6 wk | 8.5140 | 8.5122 | −0.002 | 7 | No visible corrosion |
| Comercial NaAc | Bare Metal | 1 wk | 8.5855 | 8.5841 | −0.001 | 7-8 | Very slight visible corrosion |
| Comercial NaAc | Bare Metal | 1 wk | 8.4375 | 8.4368 | −0.001 | 7-8 | Very slight visible corrosion |
| Comercial NaAc | Bare Metal | 3 wk | 8.2110 | 8.2106 | 0.000 | 7-8 | Very slight visible corrosion |
| Comercial NaAc | Bare Metal | 6 wk | 8.2827 | 8.2821 | −0.001 | 7-8 | Very slight visible corrosion |
| API KA | Bare Metal | 1 wk | 8.5137 | 8.5128 | −0.001 | 7 | No visible corrosion |
| API KA | Bare Metal | 1 wk | 8.1972 | 8.1966 | −0.001 | 7 | No visible corrosion |
| API KA | Bare Metal | 3 wk | 8.3366 | 8.3352 | −0.001 | 7 | No visible corrosion |
| API KA | Bare Metal | 6 wk | 8.2891 | 8.2886 | 0.000 | 7 | No visible corrosion |

TABLE 1-continued

Corrosion testing against commercial deicer.

| Sample | Metal Type | Time | Start Wt (g) | 1 week Wt (g) | Difference From Start (g) | PH | Comments |
|---|---|---|---|---|---|---|---|
| API NaAc | Bare Metal | 1 wk | 8.3562 | 8.3547 | −0.002 | 8 | Very slight visible corrosion |
| API NaAc | Bare Metal | 1 wk | 8.4800 | 8.4739 | −0.006 | 8 | Very slight visible corrosion |
| API NaAc | Bare Metal | 3 wk | 8.1931 | 8.1922 | −0.001 | 8 | Very slight visible corrosion |
| API NaAc | Bare Metal | 6 wk | 8.4993 | 8.4881 | −0.011 | 8 | Very slight visible corrosion |
| H2O | Bare Metal | 1 wk | 8.2774 | 8.2758 | −0.002 | 6 | Slight visible corrosion |
| H2O | Bare Metal | 1 wk | 8.2167 | 8.2141 | −0.003 | 6 | Slight visible corrosion |
| H2O | Bare Metal | 3 wk | 8.4849 | 8.4581 | −0.027 | 6 | Some pitting |
| H2O | Bare Metal | 6 wk | 8.2183 | 8.0434 | −0.175 | 6 | Some pitting |

TABLE 2

Deicer performance in friction test.

| Fluid | Friction |
|---|---|
| dry | 0.88 |
| H2O | 0.77 |
| API KA | 0.69 |
| KA Standard | 0.66 |
| Corn Oil | 0.38 |
| Ice | 0.10 |

The performance of deicers generated was compared against standard sodium acetate and potassium acetate deicers for melting, penetration, and undercutting properties as shown below. The average melt volume values for liquids have been adjusted by 3.8 mL deicer applied.

TABLE 3

Comparison of Deicer melting.

| | | Temperature | | |
|---|---|---|---|---|
| Deicer | Time (min.) | 25° F. mL/g | 15° F. mL/g | 5° F. mL/g |
| API NaAc | 10 | 3.28 | 1.12 | 0.05 |
| | 60 | 8.35 | 4.44 | 2.36 |
| NaAc Standard | 10 | 0.56 | 0.24 | 0.02 |
| | 60 | 5.43 | 1.32 | 0.10 |
| API KAc | 10 | 2.57 | 1.42 | 0.89 |
| | 60 | 5.24 | 2.31 | 1.11 |
| KAc Standard | 10 | 2.25 | 1.15 | 0.60 |
| | 60 | 3.96 | 1.57 | 0.70 |

TABLE 4

Comparison of deicer penetration.

| | | Temperature | | |
|---|---|---|---|---|
| | | 25° F. | 15° F. Weight(mg) | 5° F. |
| Deicer | Time (min) | Penetration per mg | Penetration per mg | Penetration per mg |
| API NaAc | 10 | 0.05 | 0.01 | 0.00 |
| | 60 | 0.15 | 0.06 | 0.00 |
| NaAc Standard | 10 | 0.05 | 0.02 | 0.00 |
| | 60 | 0.12 | 0.05 | 0.00 |
| API KAc | 10 | 0.10 | 0.07 | 0.00 |
| | 60 | 0.27 | 0.15 | 0.00 |
| KAc Standard | 10 | 0.09 | 0.05 | 0.00 |
| | 60 | 0.24 | 0.12 | 0.00 |

TABLE 5

Comparison of deicer undercutting.

| | | Temperature | | |
|---|---|---|---|---|
| Deicer | Time (min) | 25° F. Undercut mm$^2$/mg | 15° F. Undercut mm$^2$/mg | 5° F. Undercut mm$^2$/mg |
| API NaAc | 10 | 0.20 | 0.19 | 0.16 |
| | 60 | 0.23 | 0.24 | 0.16 |
| NaAc Standard | 10 | 0.20 | 0.20 | 0.17 |
| | 60 | 0.28 | 0.23 | 0.17 |
| API KAc | 10 | 0.20 | 0.20 | 0.16 |
| | 60 | 0.42 | 0.26 | 0.20 |
| KAc Standard | 10 | 0.25 | 0.20 | 0.16 |
| | 60 | 0.32 | 0.26 | 0.21 |

The deicer according to Example 1 developed a precipitate. The precipitate was analyzed for the metal content. The metals originated from the wood, chemicals, and equipment used in the preparation of deicer.

TABLE 6

Inorganic metal content of the precipitate.

| | Element | | | | | | | | | | | |
|---|---|---|---|---|---|---|---|---|---|---|---|---|
| | Ca | Cr | Cu | Fe | K | Mg | Mn | Na | Ni | P | S | Si | Zn |
| % of solids | 7.8 | 2.4 | 0.3 | 17.0 | 17.1 | 1.5 | 0.4 | 0.5 | 1.0 | 0.8 | 3.4 | 0.4 | 1.0 |

Example 3

Northern hardwood liquid extract from masonite steam explosion process was collected after steaming, refining, and washing the residual wood pulp. The extract was evaporated to 4 wt % of total solids. The condensate analysis by GC-MS showed impurities including of furfural, 2-furanmethanol, and 5-methyl-2-furancarboxaldehyde.

Concentrated extract was hydrolyzed with 1 wt % sulfuric acid for 1 hour at 120° C. The hydrolyzate was further evaporated to about 15 wt % solids. The condensate analysis by GC-MS showed additional impurities: furancarboxylic acid-methyl ester, 2-hydroxybenzoic acid, vanillin, ferulic acid, pyrogallol 1,3-dimethyl ether, and fatty acids from the lignin degradation.

Upon adding potassium hydroxide to reach pH 9, the combined condensate progressively discolored due to reaction with the impurities in the solution. This solution was evaporated further to contain 50% of potassium acetate. The condensate analysis by GC-MS showed additional impurities:

acetone, methyl vinyl ketone, methyl isopropyl ketone, acetol, dimethylketol, acetonyl, acetonyl acetone, 2-cyclohexen-1-one, 4,5,6,7-tetrahydrobenzofuran-7-one, and 4-allyl-2,6-dimethoxy phenol.

Example 4

The discolored dilute condensate prepared according to Example 3 was purified through activated carbon column with varied empty bed contact time (EBCT). The purification resulted in clear liquid, composed of organic acids as shown in the Table 7 (by HPLC analysis).

TABLE 6

Organic acid content and color of condensate at pH 9.

| Specimen | Formic Acid, g/l | Acetic Acid, g/l | True Color | Apparent Color |
|---|---|---|---|---|
| Unfiltered Deicer | 0.2 | 1.503 | | 330 |
| Filtered EBCT = 2 m | 0.178 | 1.475 | 1 | 15 |
| Filtered EBCT = 3 m | 0.169 | 1.463 | 0 | 1 |

Example 5

The concentrated deicer from Example 4 was passed through activated carbon column to remove color. Clear deicer was obtained and the organic acid composition is shown in Table 8.

TABLE 8

Organic salt content of clear concentrated deicer in aqueous solution.

| Organic Salt | wt % of solution |
|---|---|
| Potassium Acetate | 50.28% |
| Potassium Formate | 8.11% |
| Potassium Lactate | 0.16% |

The formulation of the current invention provides better deicing performance compared to commercial acetate deicing solutions. Surprisingly, the performance is consistently better in all testing categories including melting, penetration, undercutting, and friction. The corrosiveness is similar to commercial deicers, which include corrosion inhibitors. The chemical analysis revealed that the potassium acetate solution contains of formic acid and lactic acid the prepared solution. It is surprising to find the formic acid in the solution, because it does not naturally exist in the biomass.

What is claimed is:

1. A process for producing a deicer composition, said process comprising:

(a) treating a biomass feedstock in the presence of an acidic, neutral, or alkaline solution to solubilize at least a portion of said biomass, thereby producing an extract liquor;

(b) adjusting the pH of said extract liquor to a selected first pH of about 4.8 or less, thereby producing an acidified extract liquor comprising acetic acid and formic acid;

(c) separating dissociated acetic acid and formic acid from said acidified extract liquor to form a dilute organic acid solution;

(d) combining said dilute organic acid solution with an alkali oxide, alkali hydroxide, and/or alkali carbonate, wherein said alkali is selected from the group consisting of potassium, sodium, magnesium, calcium, and combinations thereof, to adjust the pH to a selected second pH of at least about 3.8, thereby producing an organic salt solution comprising alkali acetate and alkali formate; and (e) concentrating said organic salt solution to a concentration of at least about 25 wt % organic salts, thereby producing a deicer composition comprising alkali acetate and alkali formate.

2. The process of claim 1, wherein said treating in step (a) comprises extraction using steam or hot water, optionally with one or more additives or catalysts.

3. The process of claim 1, wherein said selected first pH is less than about 3.8.

4. The process of claim 1, wherein the amount of said formic acid produced is varied by adjusting said selected first pH.

5. The process of claim 1, wherein said dilute organic acid solution comprises from about 0.05 wt % to about 4 wt % acetic acid and from about 0.01 wt % to about 1 wt % formic acid.

6. The process of claim 1, said process further comprising introducing an additional amount of formic acid or a formate salt and/or an additional amount of lactic acid or a lactate salt to said dilute organic acid solution or to said organic salt solution.

7. The process of claim 1, wherein said organic salt solution is concentrated in step (e) to a concentration of at least about 50 wt % organic salts.

8. The process of claim 1, wherein said organic salt solution or said deicer composition is crystallized to at least 99 wt % purity.

9. The process of claim 1, said process further comprising purification of said deicer composition to produce a purified deicer composition, wherein said purification comprises a step selected from the group consisting of ion exchange, activated-carbon treatment, filtration, crystallization, and combinations thereof.

10. The process of claim 1, wherein said deicer composition comprises said alkali formate in a concentration from about 1 wt % to about 15 wt %.

* * * * *